US012605206B2

(12) United States Patent
Mihalef et al.

(10) Patent No.: US 12,605,206 B2
(45) Date of Patent: Apr. 21, 2026

(54) ENDOVASCULAR IMPLANT DECISION SUPPORT IN MEDICAL IMAGING

(71) Applicant: Siemens Healthineers AG, Forchheim (DE)

(72) Inventors: Viorel Mihalef, North Brunswick, NJ (US); Saikiran Rapaka, Pennington, NJ (US)

(73) Assignee: Siemens Healthineers AG, Forchheim (DE)

( * ) Notice: Subject to any disclaimer, the term of this patent is extended or adjusted under 35 U.S.C. 154(b) by 1501 days.

(21) Appl. No.: 17/257,592

(22) PCT Filed: Sep. 25, 2018

(86) PCT No.: PCT/EP2018/075995
§ 371 (c)(1),
(2) Date: Jan. 4, 2021

(87) PCT Pub. No.: WO2020/064090
PCT Pub. Date: Apr. 2, 2020

(65) Prior Publication Data
US 2021/0290308 A1     Sep. 23, 2021

(51) Int. Cl.
*A61B 34/10*     (2016.01)
*G16H 50/20*     (2018.01)
*G16H 50/30*     (2018.01)

(52) U.S. Cl.
CPC ............. *A61B 34/10* (2016.02); *G16H 50/20* (2018.01); *A61B 2034/104* (2016.02); *A61B 2034/108* (2016.02); *G16H 50/30* (2018.01)

(58) Field of Classification Search
CPC .............. A61B 34/10; A61B 2034/104; A61B 2034/105; A61B 2034/374;
(Continued)

(56) References Cited

U.S. PATENT DOCUMENTS 7,596,401 B2 *   9/2009   Yankelevitz ............. A61B 6/12
                                                      600/407
8,983,809 B2 *   3/2015   Sharma .................. G16H 50/50
                                                      703/2
(Continued)

FOREIGN PATENT DOCUMENTS

CN        105184086 A     12/2015
CN        105474219 A      4/2016
(Continued)

OTHER PUBLICATIONS

Leng, X., et al. "Numerical simulation of patient-specific endovascular stenting and coiling for intracranial aneurysm surgical planning" J. Translational Medicine, 16:208 (2018) (Year: 2018).*
(Continued)

*Primary Examiner* — Jay Hann

(57)          ABSTRACT

A vascular implant decision support uses a medical imaging system. A physics-based model of the endovascular implant is used to simulate deployment in a vessel model of a patient based on medical imaging. A porosity of the deployed implant and the simulation are used to determine a value for each of one or more hemodynamic parameters to support the decision for endovascular treatment. A machine-learned network uses patient-specific information to select the endovascular implant, placement, and/or other implant configuration used to simulate deployment and/or to predict outcome from deployment for the patient. The clinician may use the decision support to select among options for implanting and/or to confirm adequacy of a plan. Various of these approaches may be used alone or in combination.

19 Claims, 6 Drawing Sheets

(58) Field of Classification Search

CPC ...... A61B 2034/101; A61B 2090/3762; G16H
50/20; G16H 50/30; G16H 30/40; G16H
50/50; A61F 2/82; G06T 19/20

See application file for complete search history.

(56) References Cited

U.S. PATENT DOCUMENTS

| | | | |
|---|---|---|---|
| 8,995,084 | B2 | 3/2015 | Tashiro et al. |
| 9,087,147 | B1 | 7/2015 | Fonte |
| 9,195,800 | B2 * | 11/2015 | Grady .................... G16H 50/50 |
| 10,290,230 | B2 * | 5/2019 | Babiker ................. G09B 5/02 |
| 10,460,204 | B2 | 10/2019 | Sauer et al. |
| 10,733,910 | B2 | 8/2020 | Neumann et al. |
| 2005/0137677 | A1 * | 6/2005 | Rush ......................... A61F 2/06 |
| | | | 623/1.13 |
| 2013/0191100 | A1 | 7/2013 | Mihalef et al. |
| 2015/0235569 | A1 | 8/2015 | Babiker et al. |
| 2017/0071671 | A1 | 3/2017 | Neumann et al. |

FOREIGN PATENT DOCUMENTS

| | | |
|---|---|---|
| CN | 106529117 A | 3/2017 |
| EP | 3142033 A1 | 3/2017 |

OTHER PUBLICATIONS

Morris, P., et al. "Computational fluid dynamics modelling in cardiovascular medicine" Heart, 102:18-28 (2016) (Year: 2016).*

Jeong, W. & Rhee, K. "Hemodynamics of Cerebral Aneurysms: Computational Analyses of Aneurysm Progress and Treatment" Hindawi Computational & Mathematical Methods in Medicine, vol. 2012, article No. 782801 (2012) (Year: 2012).*

Sun, Q., et al. "In-Vitro Verification of CFD Simulations for Predicting Flow in a Stented Aneurysm Model" IEEE Int'l Symp. on Biomedical Imaging: From Nano to Macro (2011) available from <https://ieeexplore.ieee.org/abstract/document/5872465> (Year: 2011).*

Chiastra, C., et al. "Patient-Specific Modeling of Stented Coronary Arteries Reconstructed from Optical Coherence Tomography: Towards a Widespread Clinical Use of Fluid Dynamics Analyses" J. Cardiovascular Translational Research, 11:156-172 (2018) (Year: 2018).*

Ralovich, K., et al. "Noninvasive hemodynamic assessment, treatment outcome prediction and follow-up of aortic coarctation from MR imaging" Med. Phys., vol. 42, No. 5 (2015) (Year: 2015).*

Bouillot, P., et al. "Computational fluid dynamics with stents: quantitative comparison with particle image velocimetry for three commercial off the shelf intracranial stents" J. NeuroIntervent Surg, 0:1-7 (2017) (Year: 2017).*

Chung, B. & Cebral, J. "CFD for Evaluation and Treatment Planning of Aneurysms: Review of Proposed Clinical Uses and Their Challenges" Annals of Biomedical Engineering, vol. 43, No. 1, pp. 122-138 (2015) (Year: 2014).*

[Larrabide 2012] I. Larrabide, M. Kim, L. Augsburger, M. Villa-Uriol, D. R"ufenacht, A. Frangi, Fast virtual deployment of self-expandable stents: method and in-vitro validation for intracranial aneurysmal stenting, Medical Image Analysis 16 (3) (2012) 721-730.

[Mihalef2012] V. Mihalef, P. Sharma, A. Kamen, T. Redel, An immersed porous boundary method for computational fluid dynamics of blood flow in aneurysms with flow diverters, in: ASME 2012 Summer Bioengineering Conference, American Society of Mechanical Engineers, 2012, pp. 101-102.

[Bouillot20012a] Bouillot et al, Geometrical deployment for braided stent, Medical Image Analysis, 2016.

[Appanaboyina 2011] S. Appanaboyina, F. Mut, R. Loehner, C. M. Putman, J. R. Cebral, Computational fluid dynamics of stented intracranial aneurysms using adaptive embedded unstructured grids, International Journal for Numerical Methods in Fluids 57 (5) (2008) 475493.

[Augsburger2011] L. Augsburger, P. Reymond, D. A. R"ufenacht, N. Stergiopulos, Intracranial stents being modeled as a porous medium: flow simulation in stented cerebral aneurysms, Annals of Biomedical Engineering 39 (2) (2011) 850-863.

[Bouillot20012b] Bouillot et al, Virtual-versus-Real Implantation of Flow Diverters: Clinical Potential and Influence of Vascular Geometry, AJNR Am J Neuroradiol 37:2079-86, 2016.

[Cebral 2005] J. Cebral, R. L"ohner, Efficient simulation of blood flow past complex endovascular devices using an adaptive embedding technique, IEEE Transactions on Medical Imaging 24 (4) (1989) 468-476.

[Hong2012] Hong, Bo, et al. "Effects of metal coverage rate of flow diversion device on neointimal growth at side branch ostium and stented artery: an animal experiment in rabbit abdominal aorta." Neuroradiology 54.8 (2012): 849-855.

[Itu2016] Itu, L., Rapaka, S., Passerini, T., Georgescu, B., Schwemmer, C., Schoebinger, M., Flohr, T., Sharma, P. and Comaniciu, D., 2016. A machine-learning approach for computation of fractional flow reserve from coronary computed tomography. Journal of Applied Physiology, 121(1), pp. 42-52.

[Ma2012] Ma, D., Dargush, G.F., Natarajan, S. K. Levy, E. I., Siddiqui, A. H., Meng, H., Computer modeling of deployment and mechanical expansion of neurovascular flow diverter in patient-specific intracranial aneurysms, Journal of Biomechanics 45 (2012) 2256-2263.

[Provot1995] Provot, X., Deformation constraints in a mass-spring model to describe rigid cloth behaviour. In Graphics interface (pp. 147-147). Canadian Information Processing Society, 1995.

[Wang2013] Wang, K., and S. Yuan. "Actual metal coverage at the neck is critical for flow-diverting stents in treating intracranial aneurysms." American Journal of Neuroradiology 34.3 (2013): E31-E32.

[Wang2012] Wang, Kuizhong, et al. "Correlation of aneurysm occlusion with actual metal coverage at neck after implantation of flow-diverting stent in rabbit models." Neuroradiology 54.6 (2012): 607-613.

International Search Report mailed Jun. 17, 2019 in corresponding International Patent Application No. PCT/EP2018/075995.

* cited by examiner

■ Structural constraint

■ Shear constraint

■ Bending constraint

Packing Here

110

112

114

Scanner

Decision Support Processor

Memory

ML Classifier

Display

113

116

ENDOVASCULAR IMPLANT DECISION SUPPORT IN MEDICAL IMAGING

CROSS-REFERENCE TO RELATED APPLICATIONS

This application is a national phase filing under 35 U.S.C. § 371 of International Patent Application No. PCT/EP2018/075995, filed Sep. 25, 2018, the disclosure of which is incorporated herein by reference in its entirety.

BACKGROUND

The present embodiments relate to endovascular implant planning. Clinicians face an increasing number of choices when treating endovascular pathologies and have to integrate multiple sources of information for planning the procedures. For instance, for patients with aneurysms, the choices could be coiling the aneurysm or placement of any one of different models of flow diverters with multiple possible implantation configurations. The clinician decides if implantation of endovascular devices like flow diverters or stents would be beneficial to the patient, and if so, make an optimal choice of the device type and its parameters (e.g. diameter, length, porosity, metal coverage area, material mechanical properties, etc.). In the case of patients with aneurysms, many patients frequently end up requiring multiple flow diverters (e.g., overlapping or extending into different outlet branches). So, the decision also has to consider whether the patient might require multiple devices, as well as their optimal placement.

Deployment of virtual stents and flow diverters has been modeled. A graphics-based approach maps the stent geometry to a cylinder as a texture map and deforms the texture map together with the cylinder deformation. Other approaches model the stent as a simplex and use external deformation forces to derive the stent implantation. These methods forgo imposing boundary conditions from the vessel or use ad-hoc external forces and internal stresses, which may not correspond with the mechanical properties of the stent. A similarly automatic, fast but purely geometric method is implemented based on Hermite spline fitting. An interactive bending method uses the commercial software Rhinoceros 4.0. A complete explicit representation of the mesh and the Finite Element Analysis method is computationally expensive. An open torus model driven geometric approach only applies to braided stents.

SUMMARY

By way of introduction, the preferred embodiments described below include methods, systems, instructions, and non-transitory computer readable media for vascular implant decision support using a medical imaging system. A physics-based model of the endovascular implant is used to simulate deployment in a vessel model of a patient based on medical imaging. A porosity of the deployed implant and the simulation are used to determine a value for each of one or more hemodynamic parameters to support the decision for endovascular treatment. A machine-learned network uses patient-specific information to select the endovascular implant, placement, and/or other implant configuration used to simulate deployment and/or to predict outcome from deployment for the patient. The clinician may use the decision support to select among options for implanting and/or to confirm adequacy of a plan. Various of these approaches may be used alone or in combination.

In a first aspect, a method is provided for vascular implant decision support using a medical imaging system. The medical imaging system scans a patient, providing data representing a vessel of the patient. A fit of a lattice of connected nodes in a regular grid to the vessel as represented in the data is simulated. The nodes have assigned masses and constraints, and the masses and constraints are from a fit of the lattice to the vascular implant. A porosity of the vascular implant in the vessel of the patient is determined based on the lattice resulting from the simulating. A hemodynamic quantity is calculated from the porosity and a fit of the vascular implant to the vessel as represented in the data resulting from the simulating. A machine-learned network predicts an outcome for the patient based on the hemodynamic quantity and based on the fit of the vascular implant to the vessel. The outcome is displayed.

In a second aspect, a method is provided for vascular implant decision support using a medical imaging system. The medical imaging system scans the patient, providing data representing a vessel of the patient. A machine-learned network selects the vascular implant and placement of the vascular implant based on the data representing the vessel of the patient. Deployment of the selected vascular implant in the vessel is simulated. A hemodynamic quantity is calculated from a model of the vascular implant as deployed in the vessel of the patient from the simulation. The hemodynamic quantity is displayed.

In a third aspect, a method is provided for vascular implant decision support using a medical imaging system. The medical imaging system scans a patient, providing data representing a vessel of the patient. Deployment of an endovascular device within the vessel is modeled based on physics. A value of a hemodynamic parameter resulting from the deployment as modeled is determined. The value is displayed.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A decision support system is provided for endovascular procedure planning. The decision support provides automatic optimization and/or guidance of decisions, such as to test outcome (e.g., flow) for selected implant plan and/or to assist is selection of the implant plan.

Aneurysm treatment planning in clinical practice depends on acquiring suitable medical images describing the pathologic vascular region. Based on the imaging data in combination with patient demographics (age, gender, weight, body mass index, etc.), past medical history (diabetes, current list of medications, previous stroke, etc.) and/or blood biomarkers (e.g., blood counts, clotting factors, hematocrit, blood viscosity, glucose level, etc.), a patient-individualized treatment strategy is set up and performed. The decision support for the treatment planning process is based on a systemic analysis of the above-mentioned factors along with simulated treatment of the patient's aneurysm using a virtual implantation of a flow-diverting stent. Only the data acquired prior to the treatment planning (medical images, blood biomarkers, patient medical history and demographics) is used for further processing. The model may also utilize simulated outcomes using machine learning or physics-based simulators, such as computational fluid dynamics models. For such simulations, an anatomical model may be extracted using either manual, semi-automatic or automatic segmentation algorithms. The virtual deployment system is integrated into the decision support.

Figure 1:
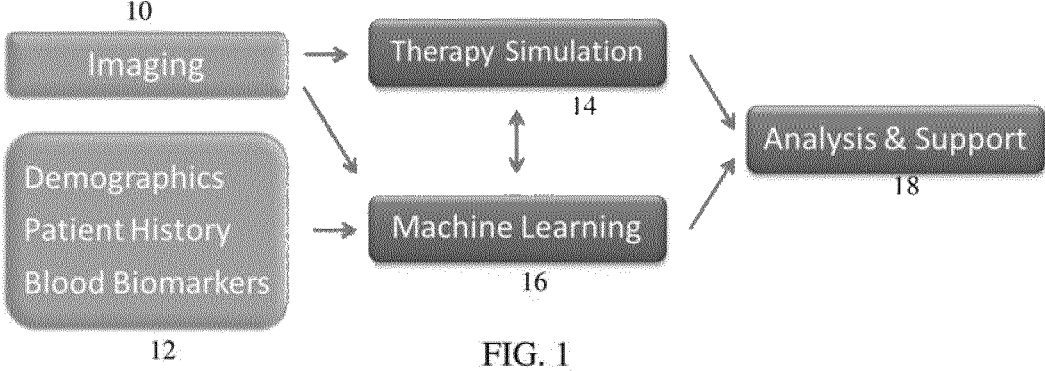
FIG. 1 illustrates a flow chart diagram of one embodiment of a method for endovascular implant clinical decision support.

FIG. 1 shows a flow chart or outline of one embodiment of the decision support for endovascular procedure planning. The outline illustrates a workflow, including device modeling (fitting the device characteristics to a physics model), deployment of the device model in a representation of the vessel of the patient, and outcome prediction based on the deployment.

In stage 10, the patient is imaged. The imaging is used to form a model of the vessel of the patient, such as segmenting a boundary mesh or fitting a vessel model. In stage 12, other patient-specific data (e.g., demographics, patient history, and blood biomarkers) are gathered from a patient electronic medical record, user input, and/or access to a laboratory database.

In stage 14, implantation is simulated. For a selected implant, a simulation models deployment of a physics-based model of the implant in the model of the vessel of the patient. The deployment simulation tracks deformation of the implant and the vessel. Depending upon the use case, the therapy simulation model may be a relatively fast machine-learned or reduced order model, or a more comprehensive, high-fidelity simulation. For both cases, the simulation may either be computed locally or computed on a networked machine or cluster with the results delivered over the network.

The physics-based model of the implant and the simulated deployment may account for the intrinsic parameters of the different therapy options. For instance, for flow diverter or stent deployment, the physics-based model of the implant may incorporate complex geometric forms and strut connections, not only braided devices. Further, different material properties (e.g., stress-strain relations for Nitinol, thermal properties, etc.) may be included if needed. For reduced order formulations, the models may include appropriately homogenized material descriptions. For instance, flow-diverters and stents may be represented as continuous sheets of spatially variable or uniform porosity instead of modeling each wire and strut.

In stage 16, a machine-learned network predicts outcome based on the simulated deployment, imaging data (e.g., segmented vessel), and/or other patient-specific information. The machine-learned network may be used to output implant information (e.g., type, size, placement, number of devices, configuration of device, etc.) used for the simulation in stage 14. Alternatively or additionally, the machine-learned network may be used to predict outcome or prognosis for a simulated deployment. The decision support system may be trained on outcome data, if available, to predict not only short-term physiological response, but also long-term outcomes and/or costs. The outcome or prognosis may be used to compare or select implant information, or the network directly outputs the selection.

In stage 18, the simulated deployment, predicted outcome, and/or a calculated hemodynamic characteristic based on the deployment are provided to the clinician. The information may be used to support decisions for planning an endovascular implantation.

Figure 2:
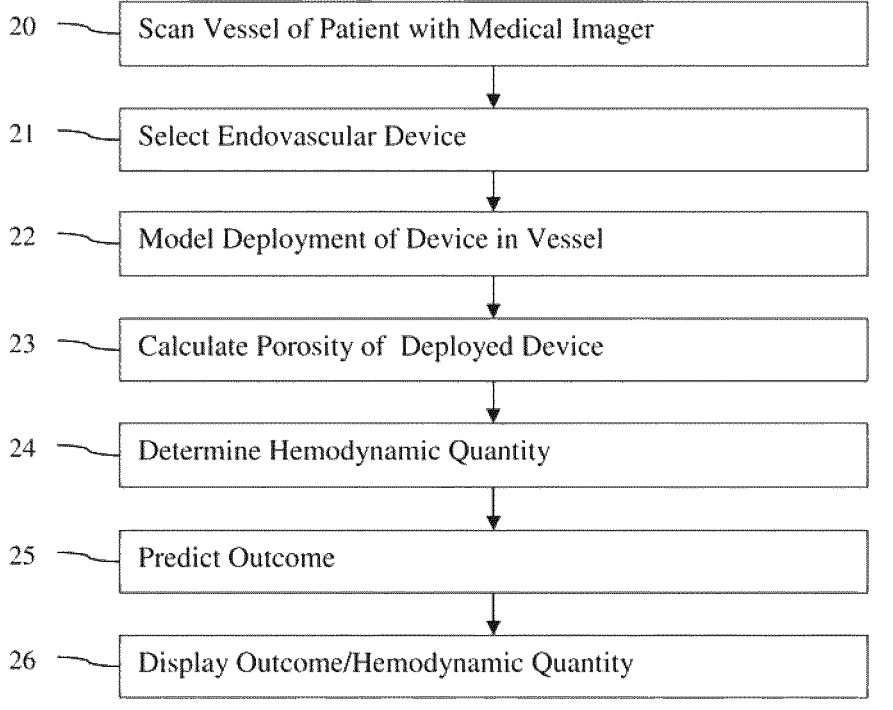
FIG. 2 is a flow chart diagram of another embodiment of a method for endovascular implant clinical decision support.

FIG. 2 is a flow chart of one embodiment of a method for vascular implant decision support using a medical imaging system. Clinical decision support is based on non-invasive medical imaging data, knowledge from machine learning, and/or other patient-specific data. The hemodynamic results from simulated deployment, selection of implant information, and/or outcome prediction are provided to a user to support decisions for planning for endovascular implantation. FIG. 2 represents an implementation of the outline of FIG. 1.

The acts are performed in the order shown (e.g., top to bottom or numerical) or other orders. For example, act 21 is performed before act 20 or as part of act 25. As another example, acts 21-25 are repeated to test different implants and/or deployments.

Additional, different, or fewer acts may be provided. For example, the method is performed without acts 23, 24, 25, and/or 26. As another example, acts for configuring a medical scanner are provided.

Figure 11:
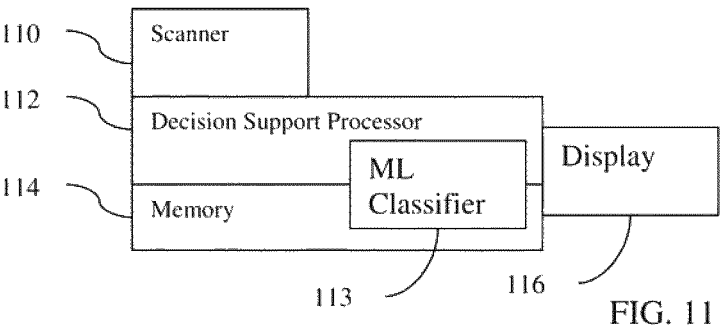
FIG. 11 is one embodiment of a system for endovascular implant clinical decision support.

The acts are performed by the system of FIG. 11 or another system. For example, act 20 is performed by medical scanner or imaging system. Acts 21-25 are performed by a decision support processor interacting with a user interface and/or a memory. In one example, the medical imaging system performs all the acts. In yet another example, a workstation, computer, portable or handheld device (e.g., tablet or smart phone), server, or combinations thereof performs one or more of the acts. The decision support system may be deployed as a standalone application on a workstation or other local computing device or as a service deployed on network (cloud) architecture (e.g., a sever connected to a client computer by a network).

In act 20, a medical imaging system scans a patient. Any medical imaging system for scanning the inside of the patient may be used, such as a computed tomography, magnetic resonance, x-ray, or ultrasound scanner.

One or more medical images or datasets are acquired. The medical image is a frame of data representing the patient. The data may be in any format. While the terms "image" and "imaging" are used, the image or imaging data may be in a format prior to actual display of the image. For example, the medical image may be a plurality of scalar values representing different locations in a Cartesian or polar coordinate format different than a display format (i.e., scan or voxel data). As another example, the medical image may be a plurality red, green, blue (e.g., RGB) values output to a display for generating the image in the display format. The medical image may not yet be a displayed image, may be a currently displayed image, or may be previously displayed image in the display or other format. The image or imaging is a dataset that may be used for anatomical imaging, such as scan data representing spatial distribution of anatomy (e.g., coronary arteries) of the patient.

The medical image is obtained by loading from memory and/or transfer via a computer network. For example, previously acquired scan data is accessed from a memory or database. As another example, scan data is transmitted over a network after acquisition from scanning a patient. In other embodiments, the medical image or scan data is directly obtained by scanning the patient.

The data represents a vessel of the patient. The vessel may or may not include branches. The heart or part of the heart may be represented. Based on the received detected intensities, a three-dimensional representation of the vessel of the patient is generated. Data representing an interior region including the vessel of a patient is obtained. The frame of data represents a three-dimensional region of the patient. Values are provided for each of multiple locations (e.g., voxels) distributed in three dimensions.

The vessel may be segmented, or other tissue masked. The segmentation provides locations of the vessel. Alternatively, boundary or another vessel detection is applied to identify the interior and/or exterior surface of the vessel. The vessel may be identified by fitting a model, such as anatomical or statistical shape model, to the scan data. A machine-learned network may detect the vessel or vessel locations from the scan data.

The vessel may be represented by a mesh. The mesh is personalized to the patient by fitting to or dividing up the surface of the segmented or identified vessel. Other representations than a mesh may be used for the vessel, such as the identified surface locations.

The mesh may be assigned characteristics to model the vessel. For example, the mesh has a linear elasticity assigned to represent response of vessel tissue to applied force. As another example, a vessel model including tissue characteristics as fit to the scan data provides the characteristics for modeling deployment. The characteristics may be default values, such as expert provided estimates, empirically determined values, values from measuring representative tissue, and/or machine-learned values. The characteristics, like the mesh, may be personalized to the patient, such as assigning elasticity characteristics of the vessel tissue based on patient age, weight and/or blood biomarkers.

Other patient-specific data may be acquired. The other patient-specific information may include genetic information, demographic information, patient history, and/or blood biomarkers. A decision support processor or other processor acquires the other patient data from a computerized medical record database or other memory. The stored information for a specific patient is accessed by look-up, mining, searching, and/or receipt over a network. Other medical equipment, such as a stethoscope, blood pressure meter, and/or laboratory diagnostics device (e.g., blood pressure, heart rate, ECG signals), may be used to provide patient data.

In act 21, the decision support processor receives a selection of an endovascular device. The selection is of a type of endovascular device, such as a flow diverter. In the following examples, a flow diverter implantation in cerebral aneurysms is used. Other endovascular devices include stents for vascular obstructions and peripheral artery disease (PAD), coiling of aneurysms, and any other device for implantation in a vessel. Other vessel conditions than an aneurysm may be treated.

The selection may include various characteristics of the device. The radius, length, porosity, material used, manufacturer, design (e.g., type of connections between struts and curvature of struts), flexibility, and/or other physical option for the device may be selected. A number of different devices may be available, each having a different construction in some way (e.g., thicker struts, different connections, different lengths, different curvatures, etc.). More than one device may be used in a given patient, so the selection may be a number of devices.

The placement of the device relative to the vessel may be selected. Starting and ending locations of the device in the vessel are selected. A region for packing may be selected. Placement of multiple devices relative to each other may be selected.

The user may select an endovascular device and/or placement. The user selects from a drop-down menu, enters a code, enters the characteristics, or otherwise makes the selection using the user interface. For placement, the user may indicate the starting and ending points on an image of the vessel or vessel model (e.g., 3D mesh rendered to 2D display image). Any locations of packing to increase porosity may be indicated. Other user inputs of the device and/or placement may be used, such as configuration for multiple devices. Alternatively, a default selection may be used.

In other embodiments, the decision support processor selects. A selection function may be used, such as relating one or more different patient-specific characteristics to characteristics of or specific ones of the available devices. In one embodiment, a machine-learned network selects the vascular implant and/or placement of the vascular implant. Any input may be used by the machine-learned network, such as basing the selection on the data representing the vessel of the patient (e.g., the scan data and/or the personalized vessel model), one or more blood biomarkers for the patient, patient history, and/or one or more demographic indicators for the patient. The machine-learned network is trained to select the endovascular device from a group of available endovascular devices, select a placement within the vessel, a configuration of the device or devices in the vessel, a number of endovascular devices, and/or other device characteristic (e.g., radius, length, and/or porosity limit (min and/or max)). Any input information may be used in training for the selection.

Machine learning uses training data as labeled or with ground truth to learn to predict the clinical decision. The training data is used as knowledge of past cases to train the network to classify the patient into decision groups or options. The training associates the features of the input vector with clinical decisions. For selection, the training associates the input information with the selection.

The decision support uses the anatomical and/or physiological knowledge using any of the different machine learning models. For training, many samples with known ground truth (e.g., selections) are used. For the samples, the machine learning model inputs may be real (from patients, or bench-scale measurements), virtual (synthetic or not representative of a given patient or physical bench arrangement), or a combination of the two. For patient data, the input samples may contain the patient images, blood biomarkers, demographics, measurements and/or genetic data. For the ground truth, the input data includes the therapy that was chosen for the patient. Other ground truths may alternatively or additionally be used, such as the recorded outcome at different temporal points (e.g., 30 days, 90 days, etc.) and/or the occurrence or lack thereof of adverse events. For the simulation or synthetic samples, a computational tool is used to produce multiple realizations of the possible patient geometry, pathological conditions, and device deployments (e.g., expert selected or computationally optimized deployment for each possible geometry and/or condition). The physics of deployment and therapy are performed on the synthetic geometries. The machine learning model is then used to learn the correspondence between the parameters of the synthetic geometries and the output selection. The initial trained model may be continuously updated using online learning or other machine learning approaches.

Any machine learning or training may be used. A probabilistic boosting tree, support vector machine, neural network, sparse auto-encoding classifier, Bayesian network, or other now known or later developed machine learning may be used. Any semi-supervised, supervised, or unsupervised learning may be used. Hierarchal or other approaches may be used. In one embodiment, the classification is by a machine-learnt classifier learnt with deep learning. As part of identifying features that distinguish between different outcomes, the classifier is also machine learnt. Any deep learning approach or architecture may be used. For example, a convolutional neural network is used. The network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided. Hierarchical structures are employed, either for learning features or representation or for classification or regression. The computer-based decision support system employs a machine learning algorithm for automated decision making.

The machine-learnt predictor, with or without deep learning, is trained to associate the categorical labels (output clinical decision of the selections) to the extracted values of one or more features. The machine-learning uses training data with ground truth to learn to select based on the input vector. The resulting machine-learnt network is a matrix for inputs, weighting, convolution kernels, and/or combinations to output a clinical decision. Using the learned network, the processor inputs the extracted values for features and outputs the selection.

The machine-learned network is trained to output a selection, outcome, risk, deployment, or other clinical support information. The information extracted from the model may include the predicted outcomes and risks under different therapy choices. The information may select the therapy configuration, such as (i) start and end locations of the flow diverter, (ii) the number of flow diverters deployed, (iii) the configuration (overlapping or deployment into different branches), (iv) the reference radius of the flow diverter to use, (v) mean and maximum porosity in the neck/non-vessel area, etc. The information output by the machine-learned network may include identification of similar patients and the therapy choices made for the similar patients identified from a patient database and their outcomes. Other outputs may be provided.

The selection of act 21 may be of a single or single set of endovascular devices, singular configuration, and singular placement. Alternatively, two or more endovascular devices, multiple configurations, and/or two or more placements are selected. A single deployment or multiple deployments for a given patient are to be modeled. The modeling may be repeated for different selections for comparison or further decision support.

In act 22, the decision support processor models deployment of the selected endovascular device within the vessel based on physics. The modeling uses the selected device and the vessel model, such as the mesh with assigned elasticity. The vessel represented by the deformable mesh and a model of the selected endovascular device are used to model deployment of the device in the vessel. Vessels are deformed by implants and/or intervention. This deformation is estimated as part of deployment. Similarly, the device is deformable, so the deformation is estimated as part of the deployment.

The deployment is modeled using physics, but a machine-learned network may be used to estimate deformation or spatial results of deployment. For the machine-learned network, deformation resulting from post-operational imaging is used as the ground truth in training. Simulations performed on a large database of real or synthetic geometries may be used for the training data.

For physics, physics-based models of the selected device and vessel are used. For the vessel, the mesh with the assigned elasticity or other representation may be used. For the selected device, a model of the specific structure is used, such as modeling the various struts, material, connections and arrangements. Rather than modeling each device differently, a simplified model fit to the devices may be used. For example, a mass-spring model is used. The same mass-spring model, but with values based on fitting to the specific structures, is used for each device.

The flow diverter or other implant device may be modeled using one of multiple representations, with arbitrary levels of physical fidelity, going from simple geometric or mass-spring models, useful for extremely fast model computations, to multi-physics models including detailed material properties and high-order (such as Finite Element) computations. A mass-spring model is used as an example, but the approach of fitting a lattice or generic model to specific devices may use other types of physics-based modeling.

Figure 3:
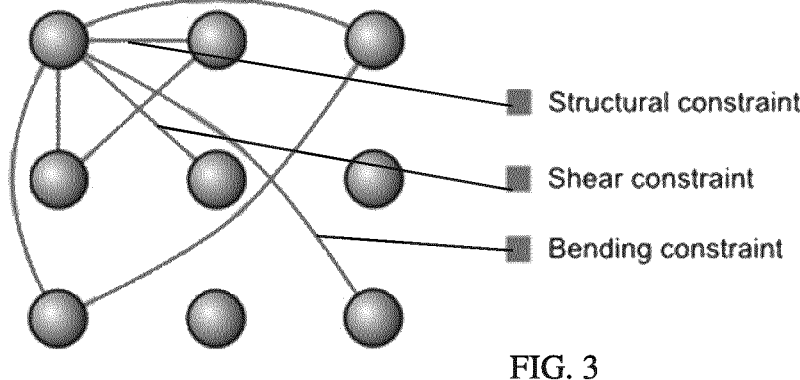
FIG. 3 illustrates an example mass-spring model for physics-based representation of different endovascular implants.

In one embodiment, the device is modeled by a lattice of connected nodes in a regular grid. The nodes have assigned masses and constraints. In the mass-spring approach, the constraints are for springs modeled as edges between the nodes. Viscoelastic or other spring representation may be used. The endovascular device is modeled as a mass-spring system, which lies upon a closed surface (topologically a cylinder) and which is comprised of a lattice whose vertices hold masses and whose edges are viscoelastic springs. The springs have prescribed stiffness constants and damping factors. For example, there are three types of springs: structural constraint springs that model resistance to out-of-plane motion, shear constraint springs that model resistance to shearing, and bending constraint springs that model resistance to bending. FIG. 3 illustrates the lattice of nodes and example constraints for one mass (i.e., node). Other arrangements may be used. The cylindrical topology of the device is implemented by, for example, enforcing periodicity of information in one of the lattice directions.

Figure 4:
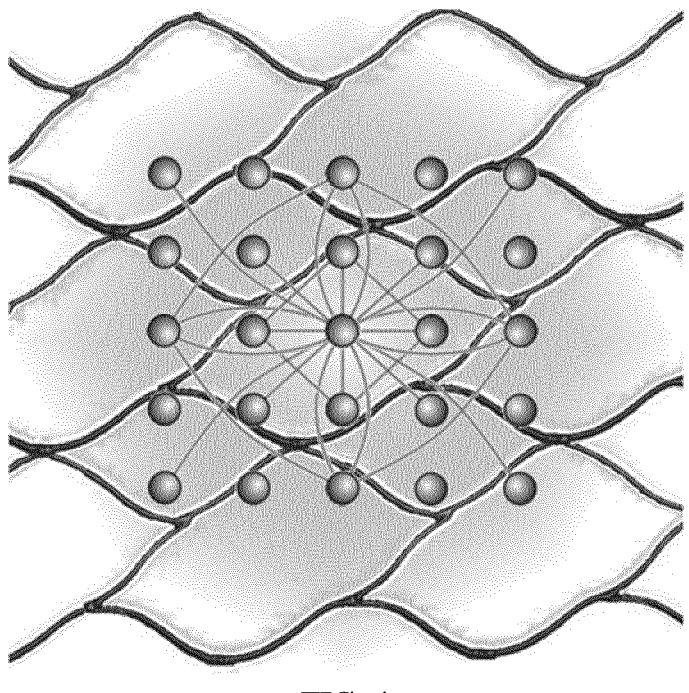
FIG. 4 illustrates an example fitting of the mass-spring model to a particular endovascular implant.

The device model is fit to the selected endovascular device. Geometric as well as functional fitting of the mass-spring or other physics model is performed. In an undeployed configuration, the lattice may be unwrapped to a flat rectangle, periodic in one direction, and initial mass, stiffness and damping properties (constant everywhere) are set. An image or representation of the "unwrapped" version of the flow diverter or other selected device is overlapped with the lattice as shown in FIG. 4. Each of the lattice vertices that is "intersected" by one of the metal struts of the selected device is tagged for personalization. Each of the lattice vertices has an associated rectangular "control box" around the node, and intersection is detected if the metal strut of the device intersects the control box. For each such tagged vertex, the mass is altered based on the length, thickness, and/or other characteristic of the strut in the control box, and the elasticity constants of the springs connected to that vertex are defined as functions of the angles made with the metal strut. This type of geometric fitting allows fast initialization of a real mechanical simulation system, even for complex geometries. The same approach may be used for various geometries of devices. The fitting of the lattice is a rasterization of the selected device so that any selected device may be represented by the same regular grid with masses and constraints assigned based on the given device.

For functional fitting, the mass-spring system is initialized using the physical mass of the real flow diverter, which is distributed to the lattice point masses. If stiffness information for the device material is available, the stiffness is used to initialize the stiffness constants. Default stiffness constants may be used. The stiffness constants may be refined by optimization that minimizes an energy function dependent on goodness-of-fit features between the output of a simulated deployment with a real device deployment. Any goodness-of-fit measure may be used, such as a geometric error metric or a specialist score (e.g. a clinician assessment of an excellent or a poor match with a real deployment). The goodness-of-fit measure may be a qualitative measure or quantitative measure (e.g., distance maps between the device and the vessel wall). A large number of such simulations may be used to train a machine learning system for learning these parameters, so the machine-learned network outputs the mass and/or constraints to be used for different nodes given an input characterization of the selected device.

The device model is used to simulate deployment. The masses, springs, and constraints from the fit of the lattice to the vascular implant are used with the vessel model to simulate a fit of the lattice of connected nodes in a regular grid to the vessel as represented in the scan data. The lattice or other physics model of the vascular implant and the 3D deformable mesh model of the vessel are used to simulate deployment. The deployment results in deformation of the device and the vessel, so the lattice and the 3D mesh are deformed as part of modeling deployment.

Any physics-based simulation may be used, such as Finite Element. Any force on a mass particle (internal viscoelastic or external like balloon, crimping or bending forces) is changed into acceleration and integrated explicitly over a time step, using for example Verlet integration, to find the new particle position. For fast collision handling, a level set may be used such that the vessel wall is located at the zero level. Collision detection is based on a fast computation of the level set value of a particle using interpolation. Collision handling may be performed using a friction force model or other simulation.

Figure 5:
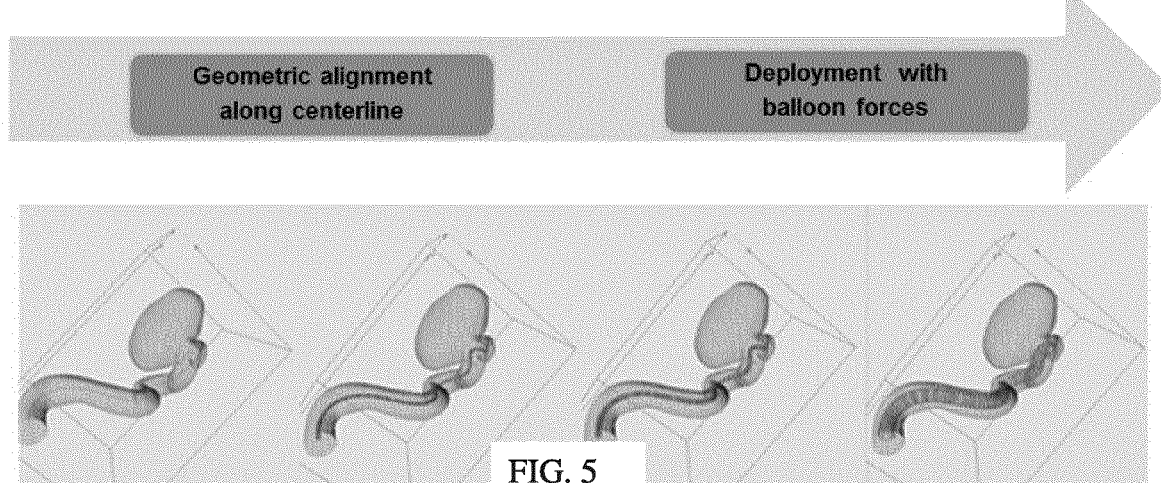
FIG. 5 illustrates a first example of simulating deployment of a mass-spring model in a patient-specific mesh for a vessel.
Figure 6:
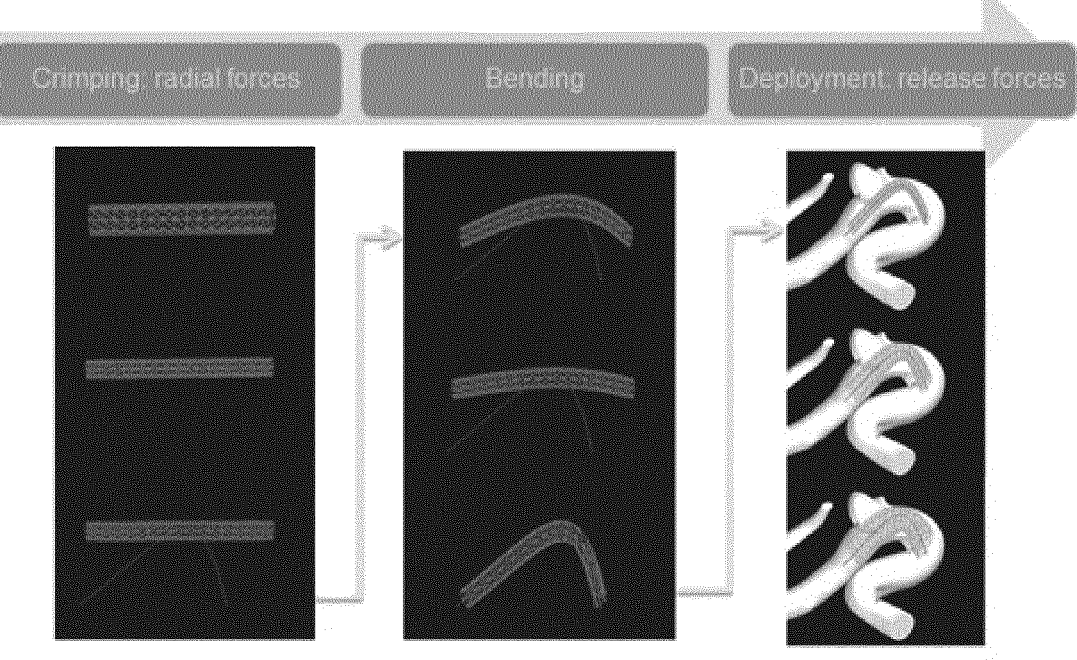
FIG. 6 illustrates a second example of simulating deployment of a mass-spring model in a patient-specific mesh for a vessel.

The deployment is simulated from an initial position of the device at the deployment placement to expansion of the device to be anchored in the vessel. In one embodiment, the centerline in the vessel lumen that extends between the cross-sectional beginning and end locations of the implant is identified. This centerline is used as a pre-deployment guide of the device. In one approach, the clinical operation is used to simulate. FIG. 5 shows a sequence where the vessel is represented, then an initial deployment along the centerline (i.e., device mesh or lattice is initialized from the centerline shape or curvature), a partial expansion of the device, and then the final anchoring of the expanded device. The expansion is modeled as inflation by balloon forces to expand and fill the lumen. FIG. 6 shows another sequence to represent simulation using memory-shape expansion. In a first stage, the implant model (lattice) is crimped or compressed from 3-5 mm to <0.5 mm diameter. In a second stage, the implant model is bent to follow the curvature of the vessel centerline. In a last stage, the release of the crimping is simulated so the implant model expands and fills the lumen. Other non-clinical-based simulation may be used, such as outputting a deployment and corresponding deformation from a machine-learned network based on inputs of the scan data, vessel model, patient-specific information, and/or device model.

Figure 7:
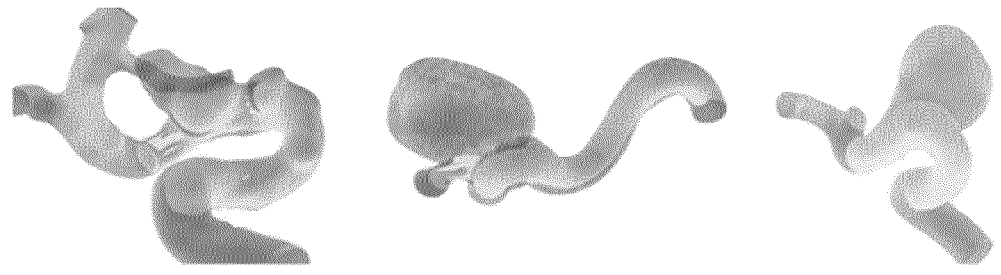
FIG. 7 illustrates example deployments in different vessel arrangements.

The simulation adapts to various endovascular devices through the fitting of the lattice of the mass-spring or other model. The simulation adapts to various vessel models based on the patient-specific scan data. FIG. 7 shows three examples of the variation in vessel curvature and structure. The physics-based simulation handles the variation with the standard grid of the lattice to simplify computation.

In act 23, the decision support processor calculates a porosity of the endovascular device from the deployment. For the flow diverter or other implant, the porosity, in part, controls the flow. In-situ implantation may produce variations in the metal coverage ratio (MCR) and porosity of the device, especially in the aneurysm and adjacent regions. Hemodynamics is consequently affected by such regions, so porosity is a consideration when performing the implantation. By simulating deployment, the porosity that results in general or by location may be determined for estimating outcome. In one embodiment, the porosity is determined as a continuously differentiable field as part of the simulation. The porosity is determined from the lattice or model of the device as deployed or resulting from the simulation.

In one embodiment, variable-porosity of the flow-diverter or other implant is modeled. The mass-spring model deployment approach enables the computation of a variable porosity component on the deployed device surface. The porosity of the diverter may be modeled as a continuously differentiable field on the device surface. The porosity of the undeployed diverter is initialized to the default manufacturer specifications using the formula porosity $f=1-MCR$ (metal coverage ratio). The change in the porosity value at a point is computed at any time step of the deployment as the local change in the surface area, given by the determinant of the Jacobian of the deformation field for the lattice. The deformation is computed for each polygonal "cell" (surface mesh triangle of the lattice) as the triangle area percentual change, clamped to an allowable percentage interval (i.e., min and max), which may be set to a subinterval of [0,1]. The local density of nodes is used in other embodiments. Depending on the needs of the subsequent uses of the porosity map, the porosity values are mapped by interpolation onto the vertices of the device (i.e., lattice model is converted back to the model of the actual device).

Figure 8:
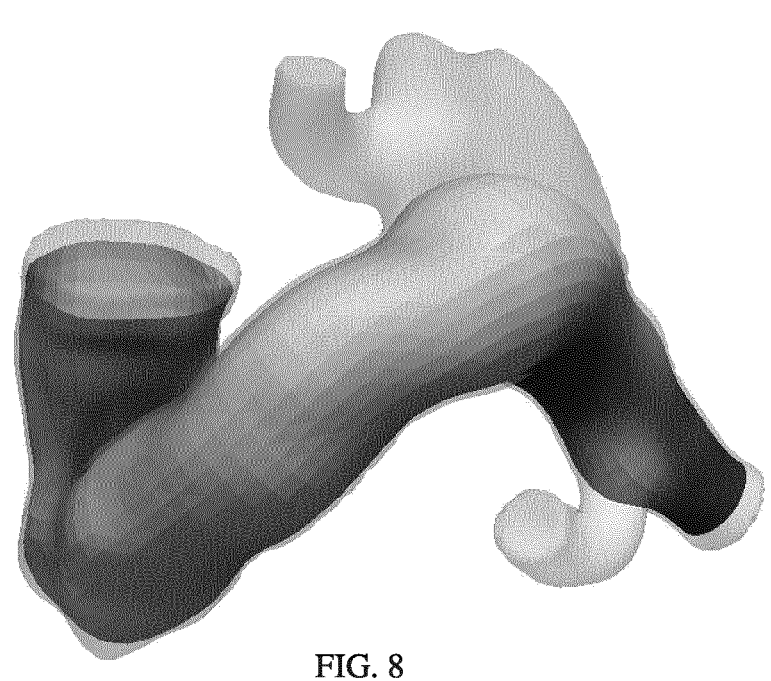
FIG. 8 shows example porosity variation resulting from deployment.

FIG. 8 shows an example rendering of a deployed lattice model in a vessel model. The grayscale of the lattice is mapped to porosity so that lighter shades correspond to higher porosity. After device deployment, the porosity may change considerably from the default or original value.

In act 24, the decision support processor determines a value for each of one or more hemodynamic parameters. The hemodynamics for the vessel change due to the deployment. The simulation of the deployment is used to calculate one or more hemodynamic quantities.

The quantity is based on the shape of the vessel as deformed. The quantity may be based on the porosity and/or variation in porosity of the simulated endovascular device. The hemodynamic quantity is calculated from the model of the vessel and the model of the vascular implant as deployed in the vessel of the patient from the simulation. The calculation is based on the deformations from the simulation. The porosity and fit of the vascular implant to the vessel as represented in the data resulting from the simulating is used. The surface of the device may be modeled as a thin porous sheet that provides a resistance to flow. The porous region may be modeled using a Darcy flow model characterized by linear and quadratic resistance coefficients.

The hemodynamic calculation uses computational flow dynamics. The input and/or output flow and pressure may be default values or values based on patient-specific information. A lumped or other simplified model may be used to represent the hemodynamics for the input and outputs to the vessel. In alternative embodiments, a machine-learned network outputs the hemodynamic quantities based on the deployment and porosity.

The output from a computational flow dynamic simulation may include flow, pressure, wall shear stress, and/or other information for many locations throughout the vessel. To simplify the analysis and to enable clinicians to develop and test clinical hypotheses, one or more hemodynamic indicators are derived as the hemodynamic quantities from the available hemodynamic information. For example, the flow, pressure, and/or shear at an aneurysm are determined. Other example hemodynamic quantities are given in the tables 1-3 below:

TABLE 1

| Quantities defined on vessel surfaces | |
| --- | --- |
| TAWSS-Mean | Spatial mean of the time-averaged WSS |
| TAWSS-Max | Spatial maximum of the time-averaged WSS |
| OSI | Oscillatory Shear Index |
| DeltaE | Energy loss between the inlet and outlet sections |
| P-Mean | Mean time-averaged pressure |
| P-Max | Maximum time-averaged pressure |
| DeltaP-Mean | Mean pressure loss between the inlet and outlet sections |
| DeltaP-Max | Maximum pressure loss between the inlet and outlet sections |
| V-Mean | Mean velocity |
| V-Max | Maximum velocity |

TABLE 2

| Quantities defined on the aneurysm | |
| --- | --- |
| TAWSS-Mean | Spatial mean of the time-averaged WSS |
| TAWSS-Max | Spatial maximum of the time-averaged WSS |
| OSI | Oscillatory Shear Index |
| P-Max | Maximum pressure, relative to mean surface averaged pressure |
| P-Mean | Mean pressure |
| SA | Surface area of the aneurysm |
| D-eff | Effective neck diameter |
| V-Max | Maximum velocity in the aneurysm |

TABLE 2-continued

| Quantities defined on the aneurysm | |
| --- | --- |
| V-Mean | Mean velocity in the aneurysm |
| E-peak | Maximum energy in the aneurysm |
| E-mean | Mean energy in the aneurysm |

TABLE 3

| Quantities defined on user-selected planes | |
| --- | --- |
| TAWSS-Mean | Mean time-averaged WSS |
| TAWSS-Max | Maximum time-averaged WSS |
| OSI | Oscillatory Shear Index |
| P-max | Maximum pressure |
| P-mean | Mean pressure |
| SA | Surface area |
| V-max | Maximum velocity |
| V-mean | Mean velocity |

Additional, different, or fewer hemodynamic quantities may be used.

Figure 9:
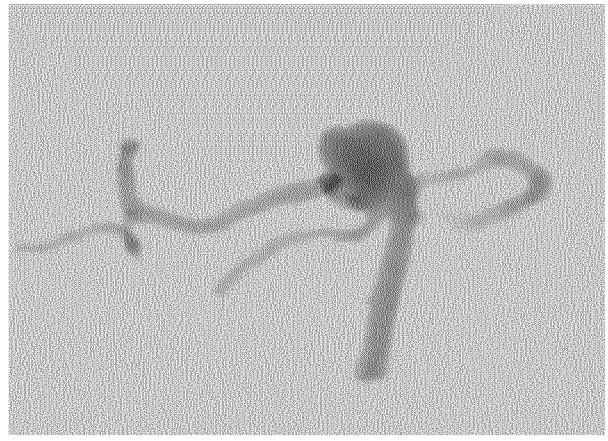
FIG. 9 is an example angiograph generated from the modeled deployment.

In an optional act, the decision support processor or a graphics processing unit generates an angiography image. Since physicians or radiologists use angiography to view the outcome and/or judge success of an implantation, an angiography image generated from the simulation of implantation may assist in deciding whether an implantation plan will have the desired outcome. To enable easy comparison of pre-treatment and post-treatment hemodynamics, a virtual angiography is implemented. The VA model takes as an input the velocity fields produced by the computational fluid dynamics solver and solves an advection-diffusion equation for the dynamics of the contrast agent. The contrast agent distribution alone (i.e., without tissue) may be used as the angiography. FIG. 9 shows an example contrast distribution as the angiography.

The angiography image may include tissue information. The view of the vessel as deformed is created by spatial shifting based on the deformation field in an image from the scan data. Alternatively, a model of an x-ray system and the scan data or deformed vessel mesh are used to emulate angiography of the tissue. The contrast agent information is added to the image of the tissue, providing the virtual angiography. Alternatively, the model of the x-ray system uses the scan data or mesh and contrast agent distribution to generate the angiography.

In act 25, the decision support processor determines an outcome. The outcome may be a clinical decision. For example, the outcome may be acceptance of a selected endovascular device or placement. The outcome may be a risk, such as a risk of rupture. The outcome may be a prognosis, such as a prediction of recovery. The prognosis may be a probability or estimate of reoccurrence within a given period. By providing the prognosis based on simulation, an estimate may be provided prior to implantation and without waiting for months after implantation. The outcome may be a hemodynamic quantity, such as the % flow to each vessel branch.

The outcome may be updated after actual implantation. The patient is scanned again. The scan is used to provide hemodynamic information for the patient, which is used to update the outcome (e.g., update prognosis).

The outcome may be determined from the hemodynamic quantities, porosity, and/or simulated deployment. The simulated treatment or information derived from the simulated treatment is used to determine the outcome if the treatment were to be used. Other patient-specific information, such as the scan data, patient history, demographics, blood biomarkers, and/or genetic information may be used to determine the outcome.

The outcome is determined using a look-up table, relational table, or function. In one embodiment, the outcome is determined by a machine-learned network. The machine-learned network predicts the outcome for the patient based on the input information (e.g., hemodynamic quantities, one or more blood biomarkers for the patient, demographic information for the patient, patient history information, and simulated fit from deployment). For example, the machine-learned network outputs a risk or prognosis for the selected vascular implant. The machine-learned network is trained based on outcomes for other patient samples and/or synthetic data.

The machine-learned network may be the same or different network used for selection. The training data may be the same or different, with the ground truth being the outcome to be predicted.

The outcome is used to assist in decision support for treatment of the patient. Other information may be used to assist in decision support, such as the hemodynamic quantities, an image of the simulated deployment results, a generated virtual angiography, and/or porosity information.

In act 26, the decision support processor generates an image, and a display screen displays the image. The output (e.g., outcome, hemodynamic quantity, porosity, visual depiction of the deployment or end result of deployment, or combinations thereof) is transmitted to a display. The output may be transmitted to a memory, such as a database of patient records, or to a network, such as a computer network. The outputs may be used to prepare an automatic, structured report and/or be added to a PACS system. The outputs may be inputs into a higher-level machine learning system or machine-learned network for patient risk assessment and scoring, outcome assessment, follow-up scheduling, etc.

The displayed hemodynamic quantity (e.g., values for multiple hemodynamic parameters), image showing placement of the vascular implant as deployed relative to the vessel from the simulation, and/or outcome provides information for the physician decisions. The clinical decision support provides an initial or starting recommendation, which may be approved or disapproved by the treating physician. The physician accesses the recommended treatment from memory, such as the patient record, and/or from a display.

In one embodiment, the clinical decisions are visualized, either as text or in a graphical way (e.g. overlaid on the medical images) and presented to the clinician. Decision support information, such as treatments, risks, guidelines, or other information, may be output. Diagnostic rules for treatment, such as based on guidelines or studies, may be output as decision support.

Any display of the decision or decisions may be used. In one embodiment, a decision tree shows the clinical decision, other possible decisions, and further treatment options resulting from the clinical decision. Besides a basic text-based display, another option is to display in a hierarchy not only the currently selected clinical decision but also possible subsequent clinical decisions.

The displayed image from the deployment simulation may be used to visually guide the placement of the device or devices. For instance, the imaging during the procedure may utilize the output to overlay planes for the start and end locations of the flow diverter to aid in device placement. Further, the live imaging data during implantation may be used to suggest if the flow diverter needs to be packed in with a higher density or if additional diverters may be required. The simulation may be performed during implantation to guide decisions for modification as the implantation occurs.

Figure 10:
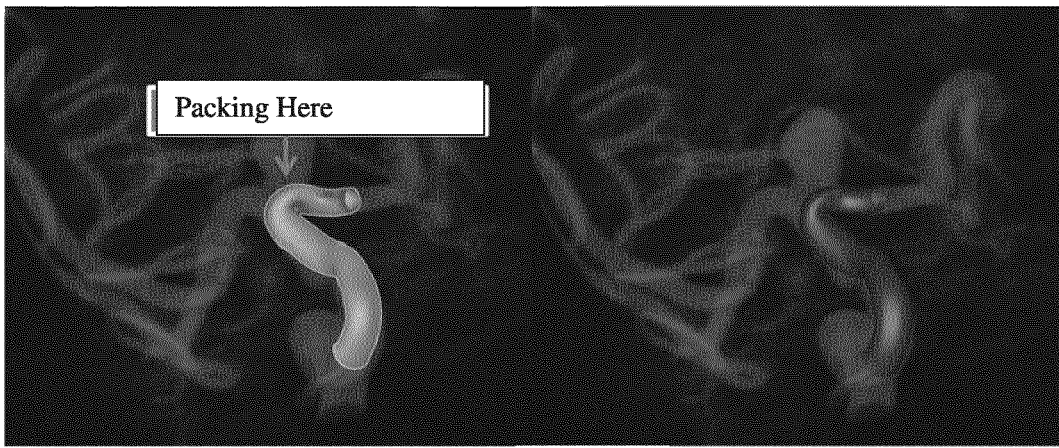
FIG. 10 shows example decision support regarding implantation based on the simulation of deployment.

FIG. 10 shows an example image generated from simulation of deployment. The simulation uses scan data for planning and/or scan data from during deployment. The simulation may be used to determine porosity, which may be used to determine hemodynamic quantity. It may be determined that lesser porosity is desired at a given location, so that location is indicated for packing. The physician may deploy the endovascular device so that lesser porosity is provided at a given region. Interactive clinical support is provided, such as where porosity values are found to be too high in an aneurysm neck region (left image). The extra packing message is relayed to the clinician. The results of the fix may be displayed (right image).

The intra-procedural image information may be used to adapt the model computations to obtain more accurate, real-time predictions. During implantation, updated scan data shows the current state of deployment and/or the vessel. This information may be used to refine the simulation, update hemodynamic quantity, update porosity, and/or update outcome. This updated output may be useful, such as accounting for any changes in the patient state since the pre-procedure imaging and/or to provide more accurate decision support output (e.g., based on greater resolution scan data from the angiographic or intra-procedure image quality).

Acts 22-25 may be repeated. The repetition may be for other vascular implants to be used for the patient. More than one endovascular device is selected, so the deployment simulation is repeated with different fits of the lattice to the different devices. The resulting porosity variation may be different for the different devices simulated in the same vessel model. The hemodynamic quantities may be different due to the different porosities and/or fits of the device to the vessel. The outcomes predicted may be different for the different devices. The different outcomes or other outputs may be displayed for comparison. The physician decides based on comparing the outputs (e.g., comparing outcomes).

FIG. 11 shows a system for endovascular implant decision support. The system implements the outline of FIG. 1, the method of FIG. 2, or another method to output recommended clinical decisions. The predicted outcome, selection, placement, hemodynamic quantities, simulated deployment, and/or porosity are output to assist a physician in deciding what implant to use for a given patient, where to place the implant, the number of implants, and/or the configuration of implants.

The system includes a scanner 110, a decision support processor 112, a memory 114, and a display 116. Additional, different, or fewer components may be provided. For example, a network or network connection is provided, such as for networking with a medical imaging network or data archival system or networking between the scanner 110 and/or the decision support processor 112. In another example, a user input and corresponding graphical user interface are provided, such as for selecting a device and/or placement. As another example, a server is provided for implementing the decision support processor 112 and/or machine-learnt classifiers 113 remotely from the scanner 110.

The decision support processor 112, memory 114, display 116, and/or machine learnt classifiers 113 are part of the scanner 110. Alternatively, the decision support processor 112, memory 114, display 116, and/or machine learnt classifiers 113 are part of an archival and/or image processing system, such as associated with a medical records database workstation or server, separate from the scanner 110. In other embodiments, the decision support processor 112, memory 114, display 116, and/or machine learnt classifiers 113 are a personal computer, such as desktop or laptop, a workstation, a server, a network, or combinations thereof.

The scanner 110 is a medical diagnostic imaging CT system. A gantry supports a source of x-rays and a detector on opposite sides of a patient examination space. The gantry moves the source and detector about the patient to perform a coronary CT angiography scan. Various x-ray projections are acquired by the detector from different positions relative to the patient. Computed tomography solves for the two or three-dimensional distribution of the response from the projections. Ultrasound, x-ray, angiography, fluoroscopy, positron emission tomography, single photon emission computed tomography, and/or magnetic resonance scanners may additionally be used.

The memory 114 may be a graphics processing memory, a video random access memory, a random-access memory, system memory, cache memory, hard drive, optical media, magnetic media, flash drive, buffer, database, combinations thereof, or other now known or later developed memory device for storing data. The memory 114 is part of the scanner 110, part of a computer associated with the decision support processor 112, part of a database, part of another system, a picture archival memory, or a standalone device.

The memory 114 stores patient data, such as in a computerized patient record. Any of the patient data discussed herein may be stored, such as scan data, fit models, parameters from fit models, measurements, clinical data, demographic information, patient history, genetic information, blood-biomarker information, non-invasive test results, and/or biochemical measurements. The memory 114 alternatively or additionally stores the machine-learned classifier 113. The memory 114 may alternatively or additionally store data during processing, such as storing information discussed herein or links thereto.

The memory 114 or other memory is alternatively or additionally a non-transitory computer readable storage medium storing data representing instructions executable by the programmed decision support processor 112 or a processor implementing the clinical decision support and/or machine-learnt classifiers 113. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The decision support processor 112 is a general processor, central processing unit, control processor, graphics processor, digital signal processor, three-dimensional rendering processor, application specific integrated circuit, field programmable gate array, artificial intelligence processor, digital circuit, analog circuit, combinations thereof, or other now known or later developed device for applying a clinical decision support for endovascular devices. The decision support processor 112 is a single device or multiple devices operating in serial, parallel, or separately. The decision support processor 112 may be a main processor of a computer, such as a laptop or desktop computer, or may be a processor for handling some tasks in a larger system, such as in the scanner 110. The decision support processor 112 is configured by instructions, design, hardware, and/or software to perform the acts discussed herein.

The decision support processor 112 is configured to select one or more endovascular devices, select placement in a vessel, model deployment of the device or devices in a patient vessel, calculate porosity variation resulting from deployment, determine values for one or more hemodynamic quantities, and predict outcome. The decision support processor 112 is configured to provide decision support for planning endovascular implantation, so may generate various outputs to assist in planning for a given patient. The machine-learned classifier or classifiers 113 may be applied to perform any one or more of the acts. Physics-based modeling, computational flow dynamics, or other modeling may be implemented by the decision support processor 112.

One or more machine-learnt classifiers 113 are provided in the memory 114 or implemented by the processor 112. For example, one machine-learnt classifier 113 is provided to select a device or devices for implanting into a patient. As another example, another machine-learned classifier 113 is provided to determine a hemodynamic value, indicate deformation from deployment, determine porosity, predict outcome, and/or other acts. Cascade, parallel, or multi-class classifiers may be used. In one embodiment, a single classifier is provided for a single decision, such as one classifier 113 to predict outcome or risk.

The decision support processor 112, using the machine-learnt classifier 113, is configured to output a clinical decision for the patient in response to the application of the input feature vector. The output of the clinical decision may be prior to entry of a treatment into the computerized patient record by a physician. The recommended decision helps guide the treating physician, so is provided to the treating physician prior to entry of an order for the patient. Alternatively, the output decision is used as the order without the intervening physician. Other timing may be provided.

The display 116 is a monitor, LCD, projector, plasma display, CRT, printer, or other now known or later developed devise for outputting visual information. The display 116 receives images of graphics, text, quantities, spatial distribution of anatomy or function, or other information from the decision support processor 112, memory 114, scanner 110, or machine-learnt classifiers 113.

One or more images are displayed. The images may or may not include anatomical representation or imaging, such as an anatomical image of the vessel from scan data, the vessel model, and/or the device model. The image includes one or more recommended decisions, such as an annotation on an image or in a display of a report for the patient. Indications of probability may be included in the image. The image includes an indication, such as a text, a graphic, or colorization, of the classification of the patient or outcome for the decision. The display may be for one specific decision. In other embodiments, the display presents to the user the top n (e.g. 3) possible decisions, ranked based on their corresponding confidence. The user may then select the final decision.

The clinical decision support system is fully automated. The recommended decisions are output once activated with no more input other than the activation. Other inputs, such as to select information (e.g., select placement of the implant) or configure the system, may be used. In an alternative embodiment, the user or clinician intervenes, leading to semi-automated decision making. For example, the clinician may select a subset of decisions that are viable or seem appropriate from a set of possible decisions. Hence, the decision support system outputs a decision from the sub-set of available decisions. Multiple machine-learnt classifiers 113 may be trained for different subsets of possible decisions, or the same machine-learnt classifier may be employed irrespective of the selected viable decisions. The decision with highest probability from the selected set of available decisions may be suggested. The clinician may intervene in the workflow by choosing to discard some of the input information or features that are considered irrelevant.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for vascular implant decision support using a medical imaging system, the method comprising:
    scanning a patient with the medical imaging system, the scanning providing data representing a vessel of the patient;
    simulating a deployment of the vascular implant using a fit of a lattice of connected nodes in a regular grid to the vessel as represented in the data, the nodes having assigned masses and constraints, the masses and constraints being from a fit of the lattice to the vascular implant;
    determining a porosity of the vascular implant in the vessel of the patient based on the lattice resulting from the simulating;
    calculating a hemodynamic quantity from the porosity and a fit of the vascular implant to the vessel as represented in the data resulting from the simulating;
    predicting an outcome for the patient based on the hemodynamic quantity and based on the simulated deployment of the vascular implant to the vessel; and
    displaying the outcome.

2. The method of claim 1 wherein scanning comprises scanning with computed tomography, x-ray, or magnetic resonance.

3. The method of claim 1 further comprising:
    repeating the simulating with different fits of the lattice to other vascular implants, repeating the determining for other porosities of different fits of the other vascular implants in the vessel, repeating the calculating of other hemodynamic quantities from the other porosities, and repeating the predicting of other outcomes from the other porosities and other fits of the other vascular implants in the vessel;

wherein displaying comprises displaying the outcome and the other outcomes.

4. The method of claim 1 wherein simulating comprises simulating with the lattice being a mass-spring model.

5. The method of claim 4 wherein simulating comprises simulating with the constraints being modeled as viscoelastic springs with the fit of the lattice to the vascular implant being based on intersections of metal struts of the vascular implant with control boxes of the nodes.

6. The method of claim 1 wherein the three-dimensional mesh is modeled as deformable so that the deployment deforms the three-dimensional mesh and the lattice.

7. The method of claim 1 wherein determining the porosity comprises determining the porosity as a continuously differentiable field as part of the simulating.

8. The method of claim 1 wherein calculating the hemodynamic quantity comprises calculating a flow or pressure with the vascular implant modeled as a porous sheet in a computational fluid dynamics simulation.

9. The method of claim 1 wherein predicting comprises predicting the outcome as a risk of rupture or prognosis.

10. The method of claim 1 wherein predicting comprises predicting based on input of the hemodynamic quantity, the fit of the vascular implant to the vessel, a blood biomarker for the patient, a demographic for the patient, and a patient history.

11. The method of claim 1 wherein displaying the outcome comprises displaying the outcome with an image showing placement of the vascular implant from the simulating.

12. A method for vascular implant decision support using a medical imaging system, the method comprising:
    scanning a patient with the medical imaging system, the scanning providing data representing a vessel of the patient;
    selecting the vascular implant and placement of the vascular implant based on the data representing the vessel of the patient;
    simulating deployment of the selected vascular implant in the vessel based on a fit of a lattice of connected nodes in a regular grid to the vessel as represented in the data, the nodes having assigned masses and constraints, the masses and constraints being from a fit of the lattice to the vascular implant;
    calculating a hemodynamic quantity from a model of the vascular implant as deployed in the vessel of the patient from the simulating; and
    displaying the hemodynamic quantity.

13. The method of claim 12 wherein selecting comprises selecting based on the data representing the vessel of the patient, a blood biomarker for the patient, a patient history, and a demographic indicator for the patient.

14. The method of claim 12 further comprising determining a risk or prognosis by the machine-learned network for the selected vascular implant.

15. The method of claim 12 wherein selecting comprises selecting the vascular implant, the placement, a number of implants, a configuration of the vascular implant, a radius of the vascular implant, and a porosity limit for the vascular implant.

16. A method for vascular implant decision support using a medical imaging system, the method comprising:
    scanning a patient with the medical imaging system, the scanning providing data representing a vessel of the patient;
    modeling deployment of an endovascular device within the vessel based on physics, the modeling based on a fit of a lattice of connected nodes in a regular grid to the vessel as represented in the data, the nodes having assigned masses and constraints, the masses and constraints being from a fit of the lattice to the vascular implant;

determining a value of a hemodynamic parameter resulting from the deployment as modeled; and displaying the value.

17. The method of claim 16 wherein modeling further comprises modeling the deployment with the vessel represented by a deformable mesh and the endovascular device represented by a mass-spring model.

18. The method of claim 16 further comprising calculating a porosity of the endovascular device from the deployment, and wherein determining the value comprises determining the value from the porosity.

19. The method of claim 16 further comprising selecting the endovascular device from a group of endovascular devices, a placement within the vessel, and a number of endovascular devices.

* * * * *